United States Patent
Zhang et al.

(10) Patent No.: US 11,406,291 B2
(45) Date of Patent: Aug. 9, 2022

(54) METHOD FOR MONITORING USER GESTURE OF WEARABLE DEVICE

(71) Applicant: Goertek Inc., Weifang (CN)

(72) Inventors: Yifan Zhang, Weifang (CN); Fuli Xie, Weifang (CN)

(73) Assignee: Goertek Inc., Weifang (CN)

(*) Notice: Subject to any disclaimer, the term of this patent is extended or adjusted under 35 U.S.C. 154(b) by 1176 days.

(21) Appl. No.: 15/762,102

(22) PCT Filed: Sep. 27, 2017

(86) PCT No.: PCT/CN2017/103637
§ 371 (c)(1),
(2) Date: Mar. 22, 2018

(87) PCT Pub. No.: WO2018/059431
PCT Pub. Date: Apr. 5, 2018

(65) Prior Publication Data
US 2019/0053738 A1 Feb. 21, 2019

(30) Foreign Application Priority Data
Sep. 30, 2016 (CN) .......................... 201610874603.3

(51) Int. Cl.
| A61B 5/11 | (2006.01) |
| A61B 5/00 | (2006.01) |
| G16H 40/63 | (2018.01) |
| G16H 50/20 | (2018.01) |
| G16H 20/30 | (2018.01) |

(52) U.S. Cl.
CPC ............ *A61B 5/1123* (2013.01); *A61B 5/002* (2013.01); *A61B 5/1114* (2013.01);
(Continued)

(58) Field of Classification Search
CPC ... A61B 5/1123; A61B 5/1114; A61B 5/6803; A61B 5/4023; A61B 5/6814
See application file for complete search history.

(56) References Cited

U.S. PATENT DOCUMENTS

| 7,383,728 B2 | 7/2008 | Noble et al. |
| 2007/0015611 A1 | 1/2007 | Noble et al. |
| 2016/0066847 A1* | 3/2016 | Sales .................... A61B 5/0022 600/324 |

FOREIGN PATENT DOCUMENTS

| CN | 1700059 A | * 11/2005 |
| CN | 103076045 A | 5/2013 |

(Continued)

OTHER PUBLICATIONS

CN 1700059 A English translation (Year: 2005).*
(Continued)

*Primary Examiner* — Allen Porter
*Assistant Examiner* — Yasmeen S Warsi
(74) *Attorney, Agent, or Firm* — LKGlobal | Lorenz & Kopf, LLP

(57) ABSTRACT

The application discloses a method for monitoring a user gesture and a wearable device. The method comprises: providing an inertial sensor in a wearable device, the wearable device being located on the head of a user when being worn; monitoring movement data of the head of the user in real time, by using the inertial sensor, when the user is wearing the wearable device; conducting gesture solving by using the movement data to obtain gesture data of the head of the user; determining whether a head gesture of the user is a correct gesture according to the gesture data and a preset strategy; and sending a reminder to the user when the head gesture of the user is an incorrect gesture.

11 Claims, 4 Drawing Sheets

(52) U.S. Cl.
CPC .......... *A61B 5/1116* (2013.01); *A61B 5/4023* (2013.01); *A61B 5/6803* (2013.01); *A61B 5/7455* (2013.01); *G16H 20/30* (2018.01); *G16H 40/63* (2018.01); *G16H 50/20* (2018.01); *A61B 5/6898* (2013.01); *A61B 5/746* (2013.01); *A61B 2503/12* (2013.01); *A61B 2560/0242* (2013.01); *A61B 2562/0219* (2013.01)

(56) References Cited

FOREIGN PATENT DOCUMENTS

| | | | |
|---|---|---|---|
| CN | 104951768 | A | 9/2015 |
| CN | 105043383 | A * | 11/2015 |
| CN | 105043383 | A | 11/2015 |
| CN | 205427703 | U | 8/2016 |
| CN | 105943052 | A | 9/2016 |
| CN | 106510719 | A | 3/2017 |
| CN | 206473327 | U | 9/2017 |
| WO | 2007008930 | A2 | 1/2007 |

OTHER PUBLICATIONS

CN 105043383 English Translation (Year: 2015).*
International Bureau of WIPO, International Search Report and Written Opinion in Application No. PCT/CN2017/103637 dated Jan. 4, 2018.

* cited by examiner

METHOD FOR MONITORING USER GESTURE OF WEARABLE DEVICE

CROSS REFERENCE TO RELATED APPLICATIONS

This Application is a U.S. National Stage entry under 35 U.S.C. § 371 based on International Application No. PCT/CN2017/103637, filed on Sep. 27, 2017, which was published under PCT Article 21(2) and which claims priority to Chinese Patent Application No. 201610874603.3, filed on Sep. 30, 2016, which are all hereby incorporated herein in their entirety by reference.

TECHNICAL FIELD

This application pertains to the field of wearable smart devices, and particularly relates to a method for monitoring a user gesture and a wearable device.

BACKGROUND

Nowadays, people use mobile telephones, personal computers and tablets more and more frequently in work and life, and many have become a "phubber". However, head dropping for a long time generates great pressure to the cervical vertebrae, impedes blood flowing in the cervical vertebrae, and causes cervical vertebrae disorders such as cervical spinal stenosis.

Presently, cervical vertebrae disorder have showed a trend of frequent occurrences and become common among urban office workers. The popularization of smart phones aggravates this trend. However, a head orientation detection system for the cervical vertebra health has not been seen yet. To add a function of monitoring cervical vertebra health is an important developing direction of smart wearable devices. In addition, other objects, desirable features and characteristics will become apparent from the subsequent summary and detailed description, and the appended claims, taken in conjunction with the accompanying drawings and this background.

SUMMARY

In view of the above problems, the application provides a method for monitoring a user gesture and a wearable device, to solve the above problems or at least partly solve the above problems.

According to an embodiment of the application, there is provided a method for monitoring a user gesture, wherein the method comprises the steps of:

providing an inertial sensor in a wearable device, the wearable device being located on the head of a user when being worn;

monitoring movement data of the head of the user in real time, by using the inertial sensor, when the user is wearing the wearable device;

conducting gesture solving by using the movement data to obtain gesture data of the head of the user; and determining whether a head gesture of the user is a correct gesture according to the gesture data and a preset strategy; and sending a reminder to the user when the head gesture of the user is an incorrect gesture.

According to another embodiment of the application, there is provided a wearable device, wherein the wearable device being located on the head of a user when being worn, and comprises an inertial sensor and a microprocessor;

the inertial sensor is for monitoring movement data of the head of the user in real time when the user is wearing the wearable device; and the microprocessor is connected to the inertial sensor, and is for conducting gesture solving by using the movement data to obtain gesture data of the head of the user, determinging whether a head gesture of the user is a correct gesture according to the gesture data and a preset strategy, and is controlled to send a reminder to the user when it is determined that the head gesture of the user is an incorrect gesture.

It can be known from the above that, in the technical solution provided by the application, the movement data of the head of the user are monitored by using the wearable device worn on the head of the user; gesture solving is conducted to the monitored movement data to obtain gesture data of the head of the user; the head gesture of the user is determined according to the gesture data and a preset strategy of the head of the user, and when the head gesture of the user is incorrect, a reminder is sent to the user. According to the technical solution, the wearable device being located on the head of the user, and the inertial sensor provided in the wearable device can maintain relatively stationary with respect to the head of the user, and can more accurately and efficiently monitor the movement data of the head of the user and further obtain more authentic gesture data of the head of the user. Thereby, the head gesture of the user can be effectively monitored by analyzing the authentic gesture data, and an alarm is sent when the gesture is incorrect to remind the user to take care of the cervical vertebra health.

BRIEF DESCRIPTION OF DRAWINGS

The present invention will hereinafter be described in conjunction with the following drawing figures, wherein like numerals denote like elements, and.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description.

In order to make the objects, technical solutions and advantages of the application clearer, the embodiments of the application will be described below in further detail in conjunction with the drawings.

Figure 1:
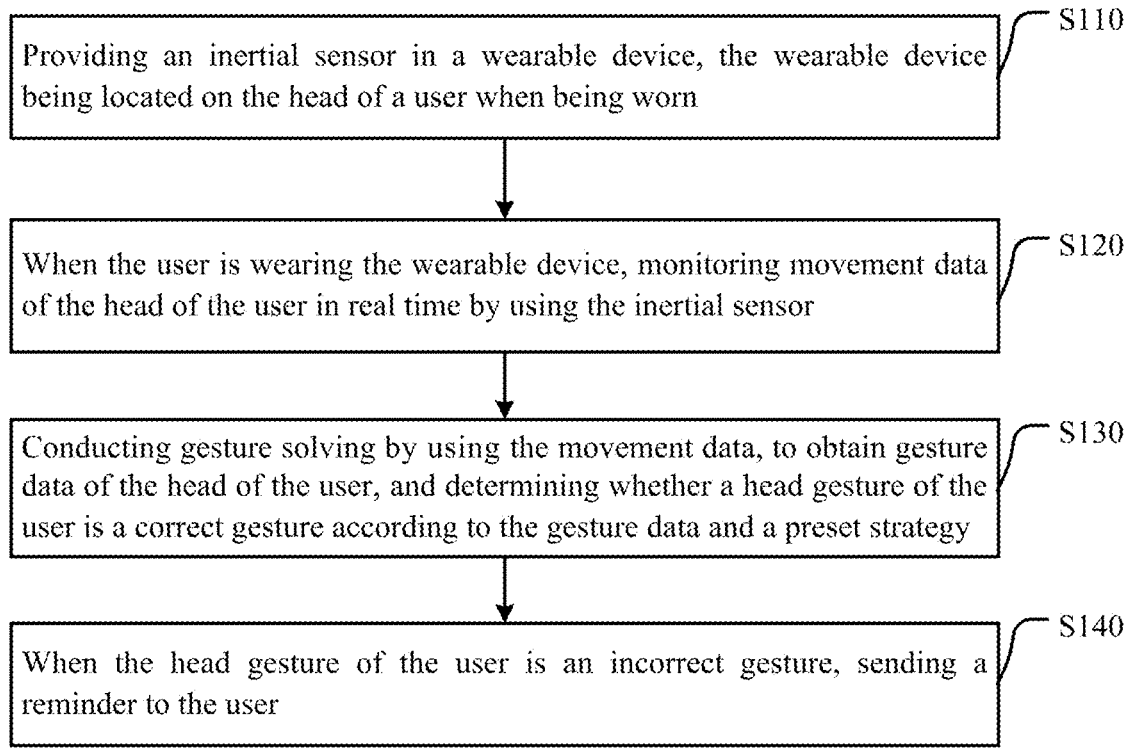
FIG. 1 shows a flow chart of a method for monitoring a user gesture according to an embodiment of the application.

FIG. 1 shows the flow chart of a method for monitoring a user gesture according to an embodiment of the application. As shown in FIG. 1, the method comprises:

Step S110, providing an inertial sensor in a wearable device, the wearable device being located on the head of a user when being worn;

Step S120, monitoring movement data of the head of the user in real time, by using the inertial sensor, when the user is wearing the wearable device;

Step S130, conducting gesture solving by using the movement data to obtain gesture data of the head of the user, and determining whether a head gesture of the user is a correct gesture according to the gesture data and a preset strategy; and Step S140, sending a reminder to the user when the head gesture of the user is an incorrect gesture.

It can be seen that, in the method shown in FIG. 1, the movement data of the head of the user are monitored by using the wearable device worn on the head of the user; gesture solving is conducted to the monitored movement data to obtain gesture data of the head of the user; the head gesture of the user is determined according to the gesture data and a preset strategy of the head of the user, and when the head gesture of the user is incorrect (gestures such as head dropping, head tilting that may result in injury to the cervical vertebra if lasting for a long duration), a reminder is sent to the user. A correct head gesture of the user refers to a gesture that does not cause injury to the cervical vertebra of the user (such as a gesture that the cervical vertebra is upward along the direction of the body or a gesture that is commonly recommended by the medical community). According to the present technical solution, the wearable device being located on the head of the user, and the inertial sensor provided in the wearable device can maintain relatively stationary with respect to the head of the user, can more accurately and efficiently monitor the movement data of the head of the user and further obtain more authentic gesture data of the head of the user. Thereby, the head gesture of the user can be effectively monitored by analyzing the authentic gesture data, and an alarm is sent when the gesture is incorrect to remind the user to take care of the cervical vertebra health.

Figure 2A:
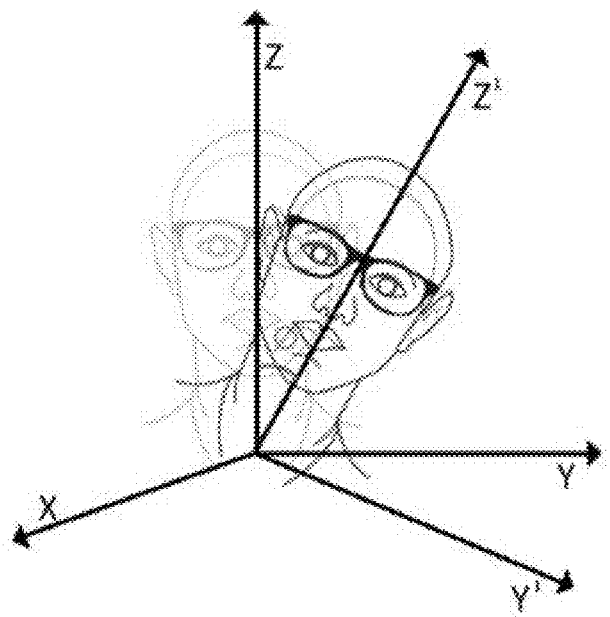
FIG. 2A shows a schematic diagram of the variation of the body coordinate system of the head of a user along with the roll rotation of the head of the user, according to an embodiment of the application.
Figure 2B:
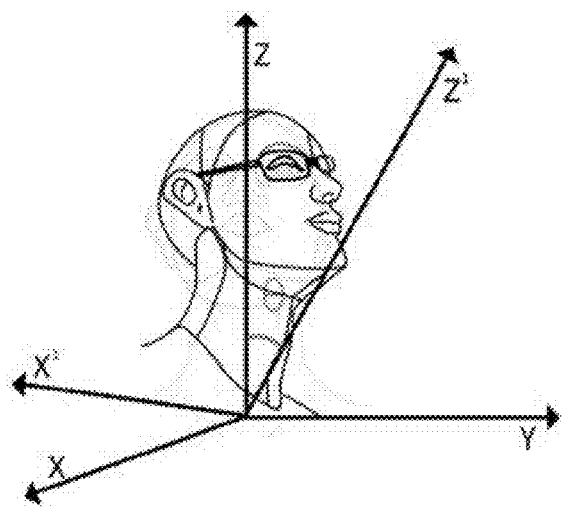
FIG. 2B shows a schematic diagram of the variation of the body coordinate system of the head of a user along with the pitch rotation of the head of the user, according to an embodiment of the application.
Figure 2C:
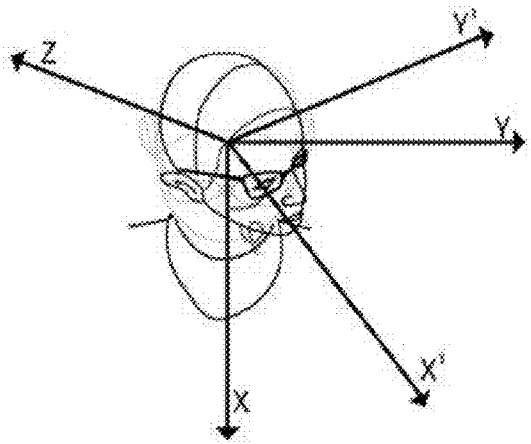
FIG. 2C shows a schematic diagram of the variation of the body coordinate system of the head of a user along with the yaw rotation of the head of the user, according to an embodiment of the application.

In an embodiment of the application, the wearable device in the method shown in FIG. 1 is smart glasses; the smart glasses comprise a spectacle frame and spectacle legs that are detachably connected to the spectacle frame, and the inertial sensor is provided in the spectacle legs. When the user is wearing the smart glasses, the spectacle legs and the head of the user are relatively stationary; namely, the inertial sensor provided in the spectacle legs moves along with the movement of the head of the user, and has a body coordinate system that is the same as that of the head of the user. In the present embodiment, x, y and z axes constitutes a body coordinate system of the head of the user, the body coordinate system varies along with movement of the head of the user, the center of the head of the user is the origin of coordinates, the forward direction of the user's line of sight is the positive direction of the x axis, and the direction that points to a center of the head top of the user is the positive direction of the z axis, and the y axis together with the x axis and the z axis constitute a right-handed coordinate system. FIG. 2A shows a schematic diagram of the variation of the body coordinate system of the head of the user along with the roll rotation of the head of the user, according to an embodiment of the application. As shown in FIG. 2A, when the head of the user performs roll rotation in the leftward and rightward direction, the body coordinate system rotates about the x axis by a certain angle, and the rotation angle is the roll angle of the head of the user. That is, the body coordinate system varies with the movement of the head of the user, and the angle between the z axis and the $z^1$ axis before and after the variation is equal to the roll angle, and the angle between the y axis and the $y^1$ axis before and after the variation is equal to the roll angle. FIG. 2B shows a schematic diagram of the variation of the body coordinate system of the head of the user along with the pitch rotation of the head of the user, according to an embodiment of the application. As shown in FIG. 2B, when the head of the user performs pitch rotation in the frontward and backward direction, the body coordinate system rotates about the y axis by a certain angle, and the rotation angle is the pitch angle of the head of the user. That is, the body coordinate system varies with the movement of the head of the user, and the angle between the z axis and the $z^1$ axis before and after the variation is equal to the pitch angle, and the angle between the x axis and the $x^1$ axis before and after the variation is equal to the pitch angle. FIG. 2C shows a schematic diagram of the variation of the body coordinate system of the head of the user along with the yaw rotation of the head of the user, according to an embodiment of the application. As shown in FIG. 2C, when the head of the user performs yaw rotation, the body coordinate system rotates about the z axis by a certain angle, and the rotation angle is the yaw angle of the head of the user. That is, the body coordinate system varies with the movement of the head of the user, and the angle between the x axis and the $x^1$ axis before and after the variation is equal to the yaw angle, and the angle between the y axis and the $y^1$ axis before and after the variation is equal to the yaw angle.

The yaw angle shown in FIG. 2C is related to the movement state of the body of the user. In the case shown in FIG. 2C, the z axis direction is parallel to the gravity vector direction, so the body coordinate system may be regarded as rotating about the gravity vector direction, namely, the geodetic coordinate system is used as the reference system, and therefore the yaw angle of the head of the user may be any angle of the user when the user is looking forward. In order to measure the yaw angle of the head of the user, it is required to obtain the movement state of the body of the user. However, by merely using the movement data obtained by the monitoring of an inertial sensor that is relatively stationary with respect to the head of the user, only the gesture information of the head of the user can be obtained, but the movement state information of the body of the user cannot be obtained. Therefore, in the process that the yaw angle of the head of the user is monitored by the inertial sensor in the spectacle legs of the smart glasses provided by the present technical solution, interference may be very easily generated, which may probably result in an error alarm when the gesture of the user is correct but the algorithm of the inertial sensor feeds back information that the gesture is incorrect, and affects the use experience of the smart glasses. For example, when the yaw angle is monitored, it cannot be determined whether the monitoring data are generated by the rotation of the body of the user or merely by the rotation of the head of the user while the body of the user does not rotate. However, unlike the yaw angle, when the user moves, his/her trunk is in the state of being perpendicular to the ground most of the time, and the rotation of the body of the user is a rotation about the gravity vector direction. The monitoring data of the roll angle and the pitch angle of the head of the user, as shown in FIGS. 2A-2B, are generated by the rotation of the head of the user about the x axis and the y axis that are perpendicular to the gravity vector direction; in other words, the rotation of the body of the user will not generate the monitoring data of the roll angle and the pitch angle. In most cases the roll angle and the pitch angle of the head of the user are only related to the movement state of the head of the user and are not influenced by the movement state of the body of the user, and the data obtained by the monitoring of the inertial sensor that is relatively stationary with respect to the head of the user can correctly reflect the roll movement and the pitch movement of the head of the user. Therefore, the roll angle and the pitch angle can reflect the correct head gesture of the user. So the technical solution provided by the application merely focuses on the roll angle and the pitch angle, to more accurately reflect the head gesture of the user.

In a particular embodiment, the inertial sensor that is provided in the spectacle legs of the smart glasses comprises an accelerometer; the Step S120 of monitoring movement data of the head of the user in real time by using the inertial sensor in the method shown in FIG. 1 comprises: measuring accelerations of the head of the user in x, y and z axis directions of the body coordinate system by the accelerometer; the Step S130 of conducting gesture solving by using the movement data, to obtain gesture data of the head of the user comprises: conducting gesture solving by using the accelerations of the head of the user in the x, y and z axis directions, to obtain a pitch angle and a roll angle of the head of the user, and using the obtained pitch angle and roll angle of the head of the user as the gesture data of the head of the user.

Particularly, the principle of conducting gesture solving by using the accelerations of the head of the user in the x, y and z axis directions obtained by the monitoring of the accelerometer to obtain a pitch angle and a roll angle of the head of the user is as follows. As is well known, the monitoring result data of the accelerometer can use the direction of the gravitational acceleration as the reference. For example, the state that the user looks forward is the initial state. At this point, the z axis direction is opposite to the gravity vector direction, and the x axis direction and the y axis direction are both perpendicular to the gravity vector direction. Accordingly, the acceleration of the head of the user in the z axis direction obtained by the monitoring of the accelerometer is equal to the gravitational acceleration, and the accelerations in the x axis direction and the y axis direction are both 0. When the head of the user moves as shown in FIG. 2A, the z axis direction varies, the y axis direction varies, and the x axis direction does not vary and is still perpendicular to the gravity vector direction. Accordingly, the acceleration of the head of the user in the x axis direction obtained by the monitoring of the accelerometer is 0, and the total acceleration that is obtained by composing the acceleration in the z axis direction and the acceleration in the y axis direction has an amplitude equal to that of the gravitational acceleration and a direction opposite to that of the gravitational acceleration. Assuming that the roll angle is $\theta$, at this point the acceleration in the z axis direction $a_z$ of the head of the user and the acceleration in the y axis direction $a_y$ of the head of the user satisfy: $a_z \cdot \cos\theta - a_y \cdot \sin\theta = g$, $a_z \cdot \sin\theta + a_y \cdot \cos\theta = 0$, wherein g is the gravitational acceleration constant, and the roll angle of the head of the user can be calculated accordingly. In a similar way, when the head of the user moves in pitch the pitch angle of the head of the user can be calculated according to the accelerations obtained by the monitoring of the accelerometer. In a similar way, when the head of the user moves in other forms, the roll angle and the pitch angle of the head of the user can both be calculated according to the accelerations obtained by the monitoring of the accelerometer.

It can be seen that, the essence of the technical solution of conducting gesture solving by using the movement data of the head of the user obtained by the monitoring of the inertial sensor to obtain gesture data of the head of the user in the above embodiment is that, according to the acceleration data of the head of the user obtained by the monitoring of the accelerometer, the rotation transformation of the body coordinate system of the head of the user with respect to the geodetic coordinate system is obtained, and then the gesture data of the head of the user is determined according to the rotation transformation of the body coordinate system. In the above embodiment, the rotation transformation of the body coordinate system of the head of the user is expressed by Euler angle method. In other embodiments, the rotation transformation of the body coordinate system of the head of the user may be expressed by gesture solving modes such as cosine matrix and quaternion method.

In another particular embodiment, the inertial sensor that is provided in the spectacle legs of the smart glasses comprises an accelerometer and a gyroscope; the Step S120 of monitoring movement data of the head of the user in real time by using the inertial sensor in the method shown in FIG. 1 comprises: measuring accelerations of the head of the user in x, y and z axis directions of the body coordinate system by the accelerometer, and measuring rotational angular velocities of the head of the user in the x, y and z axis directions by using the gyroscope; the Step S130 of conducting gesture solving by using the movement data, to obtain gesture data of the head of the user comprises: conducting gesture solving by using the accelerations of the head of the user in the x, y and z axis directions and the rotational angular velocities of the head of the user in the x, y and z axis directions, to obtain a pitch angle and a roll angle of the head of the user, and using the obtained pitch angle and roll angle of the head of the user as the gesture data of the head of the user.

Particularly, the principle of conducting gesture solving by using the accelerations of the head of the user in the x, y and z axis directions and the rotational angular velocities of the head of the user in the x, y and z axis directions, to obtain a pitch angle and a roll angle of the head of the user is as follows. As stated above, the monitoring result data of the accelerometer can use the direction of the gravitational acceleration as the reference. Namely, by monitoring the accelerations of the head of the user in the x, y and z axis directions by using the accelerometer, the position relation of the gravity vector direction and the body coordinate system of the head of the user can be obtained. However, the gyroscope can merely monitor the rotational angular velocities at which the head of the user rotates about the three axes of the body coordinate system but cannot obtain the reference direction, and thus cannot judge the accurate head gesture of the user. Therefore, as the principle of the accelerometer is indicating accelerations other than the gravitational acceleration, the direction of the gravitational acceleration can be obtained. Accordingly, the gyroscope and the accelerometer can be combined, and the gravity vector direction obtained according to the monitoring result data of the accelerometer is used as the reference direction, and the relative position relation of the body coordinate system and the gravity vector direction is determined, namely, the transformation relation of the body coordinate system with respect to the gravity vector direction is obtained. Then, integration is conducted to the rotational angular velocities about the x axis, the y axis and the z axis of the body coordinate system that are obtained by the monitoring of the gyroscope respectively, to obtain the rotation angles about the x axis, the y axis and the z axis of the body coordinate system respectively, namely, obtain the transformation relation of the body coordinate system itself. After obtaining the transformation relation of the body coordinate system itself and the transformation relation of the body coordinate system with respect to the gravity vector direction, angle transformation is conducted by a gesture solving algorithm, to obtain a pitch angle and a roll angle of the head of the user. Generally, compared with the technical solution of monitoring the movement data by the combination of the accelerometer and the gyroscope, the technical solution of monitoring the movement data by using solely the accelerometer is more suitable for the case that the movement of the head of the user is relatively slow. The reason is that the accelerometer is too sensitive to movement, and when the movement is relatively fast interferences are more easily produced in the accelerometer, which will affect the monitoring results. On the other hand, in the combination of the accelerometer and the gyroscope, only the characteristic of the accelerometer of providing the reference direction of the gravity vector is used, so the influence to the monitoring data becomes less.

It can be seen that, the essence of the technical solution of conducting gesture solving by using the movement data of the head of the user obtained by the monitoring of the inertial sensor to obtain gesture data of the head of the user in the above embodiment is that, the reference direction is determined according to the acceleration data of the head of the user obtained by the monitoring of the accelerometer, then the rotation transformation of the body coordinate system of the head of the user with respect to the geodetic coordinate system is obtained according to the reference direction and the rotational angular velocity data of the head of the user obtained by the monitoring of the gyroscope, and then the gesture data of the head of the user is determined according to the rotation transformation of the body coordinate system. In the embodiments of the application, the rotation transformation of the body coordinate system of the head of the user may be expressed by gesture solving modes such as Euler angle method, cosine matrix and quaternion method.

Figure 3:
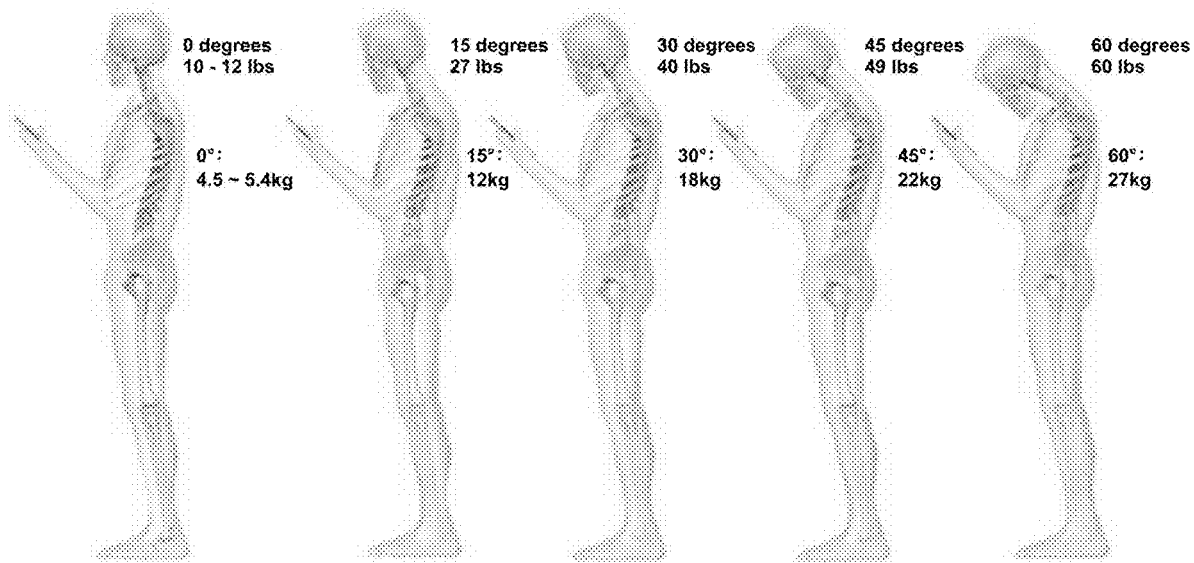
FIG. 3 shows a schematic diagram of the load weight applied to the cervical vertebra when a user is at different head dropping angles, according to an embodiment of the application.

After obtaining the gesture data of the head of the user as stated above, the method shown in FIG. 1 needs to further determine whether the head gesture of the user is a correct gesture according to the gesture data and a preset strategy. Generally speaking, when the head of the user is in dropping or tilting state for a long duration, the harm to the cervical vertebra will be great. FIG. 3 shows a schematic diagram of the load weight applied to the cervical vertebra when the user drops head at different angles, according to an embodiment of the application. It can be seen from FIG. 3 that, when the head dropping angle reaches 60°, the load weight applied to the cervical vertebra reaches over 5 times of that in straight standing, which causes tremendous burden to the cervical vertebra. Furthermore, head dropping or tilting for a long duration will result in that the outer side of the cervical vertebra is in the stretching state for a long duration, which causes diseases such as hyperostosis and severely harms the cervical vertebra health. With respect to such a situation, the Step S130 of determining whether a head gesture of the user is a correct gesture according to the gesture data and a preset strategy comprises the following technical solutions.

The first technical solution: presetting a balance threshold range; calculating a balance numerical value that indicates a balance degree of the movement of the head of the user according to the gesture data; and judging whether the balance numerical value exceeds the balance threshold range, and if yes, determining that the head gesture of the user is an incorrect gesture.

The gesture data of the head of the user obtained as stated above are the roll angle and the pitch angle of the head of the user. Generally, the ranges of the roll angle and the pitch angle of the head of the user will not exceed $[-\pi/2, \pi/2]$, and the roll angle and the pitch angle within this range may be subject to data fusion processing, to obtain a balance numerical value that identifies the balance degree of the movement of the head of the user. More particularly, the first technical solution above is that, presetting a first balance threshold range, and for each preset time cycle, accumulating each pitch angle of the head of the user that corresponds to each unit time within the preset time cycle, and using the numerical value that is obtained by the accumulating as the balance numerical value that corresponds to the pitch angles within the preset time cycle; and judging whether the balance numerical value that corresponds to the pitch angle exceeds the first balance threshold range, and if yes, determining that the head gesture of the user is an incorrect gesture; and/or, presetting a second balance threshold range, and for each preset time cycle, accumulating each roll angle of the head of the user that corresponds to each unit time within the preset time cycle, and using the numerical value that is obtained by the accumulating as the balance numerical value that corresponds to the roll angles within the preset time cycle; and judging whether the balance numerical value that corresponds to the roll angle exceeds the second balance threshold range, and if yes, determining that the head gesture of the user is an incorrect gesture. A person skilled in the art can set a balance threshold range according to the technical solution of the application in combination with a practical application scene, for example, the balance numerical value of the balance degree of the movement of the head of the user when the head dropping angle reaches 60°, or larger/smaller data, may be selected as the balance threshold range, which is not limited here.

For example, the roll angle is set negative when the head of the user tilts to the left, and positive when it tilts to the right. For each preset time cycle t, by accumulating each roll angle of the head of the user within the time range t, the balance numerical value that corresponds to the roll angle within the time t can be obtained, and the balance numerical value reflects the balance degree of the movement of the head of the user. As the tilting to the left and right of the head of the user corresponds to opposite positive and negative roll angles when reflected in data, if the balance numerical value obtained by the accumulating is smaller, it indicates that the balance degree of the movement of the head of the user is higher; on the contrary, a higher balance numerical value represents a lower balance degree of the movement of the head of the user, which indicates that the head of the user tilts to the same direction for a long duration, and it is harmful to the cervical vertebra health. If the balance numerical value exceeds a first balance threshold range, it is determined that the head gesture of the user is an incorrect gesture and a reminder is sent to the user. Similarly, the pitch angle is set negative when the user drops head, and positive when the user lifts head. For each preset time cycle t, by accumulating each pitch angle of the head of the user within the time range t, the balance numerical value that corresponds to each pitch angle within the time t can be obtained, and the balance numerical value reflects the balance degree of the movement of the head of the user. As the head dropping and lifting of the user corresponds to opposite positive and negative pitch angles when reflected in data, if the balance numerical value obtained by the accumulating is smaller, it indicates that the balance degree of the movement of the head of the user is higher; on the contrary, a higher balance numerical value represents a lower balance degree of the movement of the head of the user, which indicates that the user drops or lifts head for a long duration, and it is harmful to the cervical vertebra health. If the balance numerical value exceeds a second balance threshold range, it is determined that the head gesture of the user is an incorrect gesture and a reminder is sent to the user. If within the time t the head of the user firstly tilts to the left by a relatively large angle and then tilts to the right by a relatively large angle, the calculated balance numerical value that corresponds to the roll angle is close to 0, and accordingly it is regarded that the head of the user conducted symmetrical actions, and the stress applied to the cervical vertebra of the user is in the state of relative balance. In case that the head of the user performs both roll movement and pitch movement, the movement angles of the head of the user may be resolved into a roll angle and a pitch angle first, and then the balance numerical values that correspond to the roll angle and the pitch angle is calculate respectively according to the above method, to judge whether the head gesture of the user is correct.

The second technical solution: presetting a gesture data threshold range; judging whether the gesture data exceed the gesture data threshold range, and if yes, the head gesture of the user is determined as inappropriate; and determining that the head gesture of the user is an incorrect gesture if the inappropriate head gesture of the user maintains beyond a preset duration range.

In the above second technical solution, a preset gesture data threshold range is used to characterize a critical region where the head gesture of the user is in a state harmful to the cervical vertebra health. When the gesture data exceed the gesture data threshold range, it is determined that the head gesture of the user is in a state that is harmful to the cervical vertebra health, that is, the head gesture of the user is inappropriate. If the state of inappropriateness of the head gesture of the user maintains beyond a preset duration range, it is determined that the head gesture of the user is an incorrect gesture, and a reminder to the user is initiated. A person skilled in the art can set a gesture data threshold range according to the technical solution of the application in combination with a practical application scene, for example, the balance numerical value of the balance degree of the movement of the head of the user when the head dropping angle reaches 60°, or larger/smaller data, may be selected as the balance threshold range, which is not limited here.

If the first and second technical solutions are compared, the essence of the first technical solution is conducting dynamic accumulating calculation to the head gesture of the user, and using the comprehensive variation result within a time interval as the criteria for judging whether the head gesture of the user is correct, while the essence of the second technical solution is monitoring the inappropriate gestures in the gestures of the head of the user, and using the inappropriate gesture maintaining beyond a certain duration as the criteria for judging whether the head gesture of the user is correct. Regarding the second technical solution, because it uses the inappropriate gesture maintaining beyond a certain duration as the judging criteria, there will be misjudgments. For example, if the head of the user tilts to the left for time $T_1$ and then tilts to the right for time $T_2$, and the tilting to the left and right are both inappropriate gestures, when the sum of time $T_1$ and $T_2$ is greater than the preset duration range, it is determined that the head gesture of the user is incorrect. If the balance judging criteria of the first technical solution is used, the variations of the head of the user within a time interval are comprehensively considered, which can prevent such misjudgments.

Figure 4:
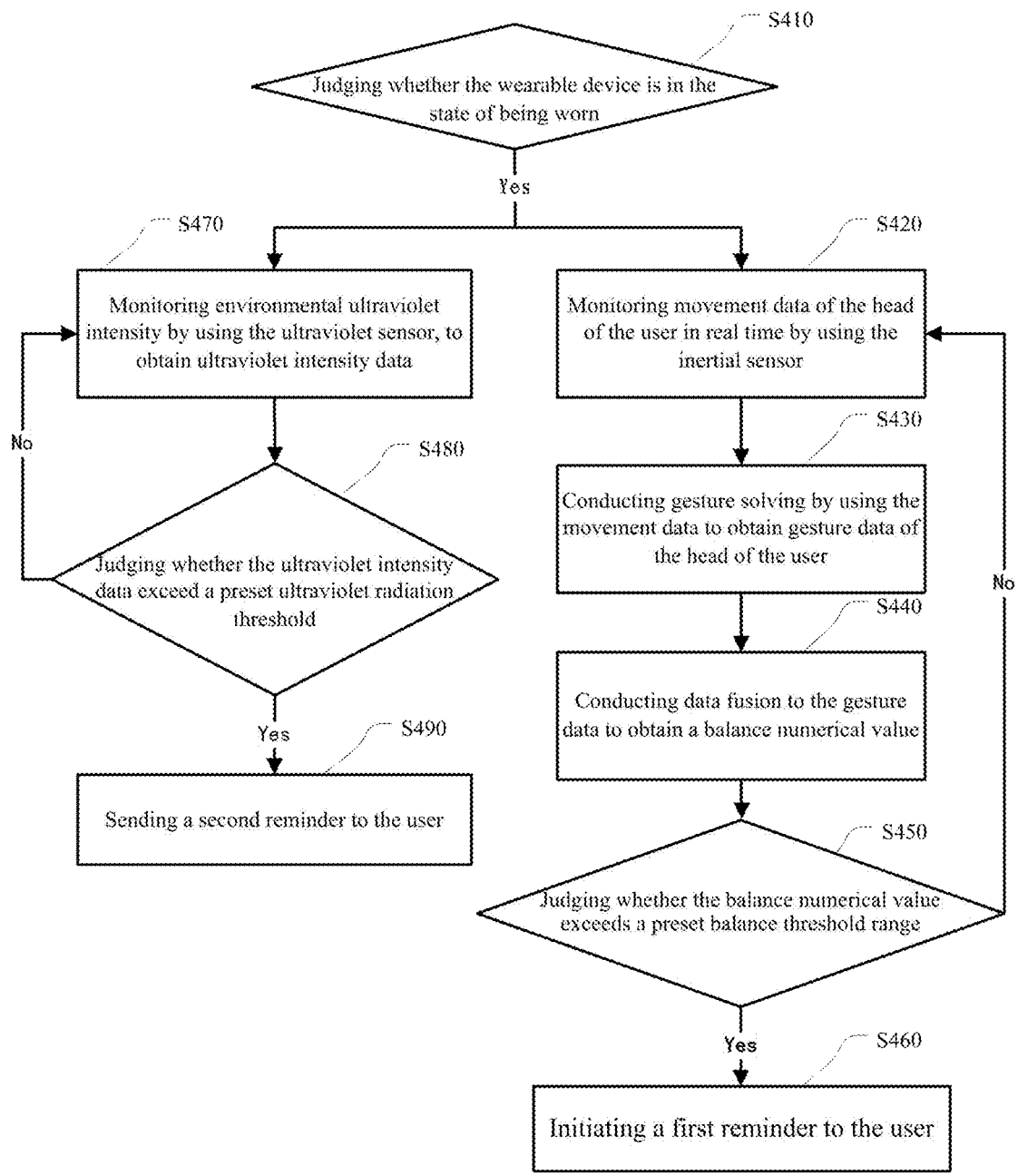
FIG. 4 shows the flow chart of a method of monitoring and alarm by using a wearable device according to an embodiment of the application.

In everyday life people may be exposed to various kinds of radiations, and excessive exposure will affect the health of human being. Ultraviolet (UV) radiations are the most common radiations in daily life and include UV-A, UV-B and UV-C. Among them, UV-C is an ultra-short wave ultraviolet ray, and basically can be completely absorbed by the earth atmosphere layer, while UV-B and UV-A can permeate the atmospheric layer and directly radiate to the ground. It is generally believed that, UV-B is a main trigger of skin cancer, and UV-A will cause skin tanning, has a certain influence on skin cancer, and will cause ocular diseases such as cataract, retinitis solaris and cornea hypoplasia. In an embodiment of the application, the wearable device is provided with an ultraviolet sensor, and the ultraviolet sensor is for monitoring environmental ultraviolet intensity, FIG. 4 shows the flow chart of a method of monitoring and alarming by using the wearable device according to an embodiment of the application. The wearable device comprises an inertial sensor and an ultraviolet sensor. It can be seen from FIG. 4 that, the method comprises:

Step S410, judging whether the wearable device is in the state of being worn, and if yes, individually executing Step S420 and Step S470;

Step S420, monitoring movement data of the head of the user in real time by using the inertial sensor;

Step S430, conducting gesture solving by using the movement data to obtain gesture data of the head of the user;

Step S440, conducting data fusion to the gesture data to obtain a balance numerical value;

Step S450, judging whether the balance numerical value exceeds a preset balance threshold range, and if yes, executing Step S460; if no, executing Step S420;

Step S460, initiating a first reminder to the user;

Step S470, monitoring environmental ultraviolet intensity by using the ultraviolet sensor, to obtain ultraviolet intensity data;

Step S480, judging whether the monitored ultraviolet intensity data exceed a preset ultraviolet radiation threshold, and if yes, executing Step S490; if no, executing Step S470; and Step S490, sending a second reminder to the user.

The technical solution of Step S410 of judging whether the wearable device is in the state of being worn may be: presetting a wearing detecting threshold; and monitoring the acceleration of the wearable device in real time by using the accelerometer, judging whether variation within a preset duration of an amplitude value of the acceleration of the wearable device exceeds the wearing detecting threshold, and if yes, determining that the wearable device is in the state of being worn. Particularly, the accelerations $a_x$, $a_y$ and $a_z$ in the x, y and z axes of the body coordinate system of the wearable device are monitored in real time by the accelerometer; the acceleration amplitude A is calculated according to the accelerations $a_x$, $a_y$ and $a_z$ in the x, y and z axes of the body coordinate system of the wearable device, such as $A=\sqrt{a_x^2+a_y^2+a_z^2}$, or $A=|a_x|+|a_y|+|a_z|$; it is judged whether the variation within a preset duration of the acceleration amplitude A exceeds a preset wearing detecting threshold, and if yes, it indicates that the wearable device moves along with the head of the user within the preset duration, and it is determined that the wearable device is in the state of being worn. By this step it is judged first whether the user has worn the wearable device before the wearable device monitors the movement data of the head of the user, so as to avoid obtaining useless data due to beginning the monitoring of data before the user wears the wearable device, and further avoid the interference to the subsequent process for determining the head gesture of the user caused by the useless data.

Furthermore, in an embodiment of the application, the wearable device is further provided with a linear motor and/or a Bluetooth communication module; when the wearable device is smart glasses, the linear motor and/or Bluetooth communication module are provided in the spectacle legs of the smart glasses. In the Step S460, after the head gesture of the user is determined as an incorrect gesture, a first reminder may be sent to the user via the vibration of the linear motor in the spectacle legs; alternatively, it may be connected to another mobile terminal via a Bluetooth communication module, and push a reminder message to the another mobile terminal. Further, in the Step S490, after the environmental ultraviolet intensity data exceed the ultraviolet radiation threshold, a second reminder may be sent to the user via the vibration of the linear motor in the spectacle legs; alternatively, it may be connected to another mobile terminal via a Bluetooth communication module, and push a second reminder message to the another mobile terminal. For example, the Bluetooth connection between the smart glasses and a mobile terminal (smart phone, smart watch and so on) is established via the Bluetooth communication module, the reminder message and/or the second reminder message is pushed to the corresponding applications of the mobile terminal, and the user is reminded to notice the cervical vertebra health and avoid exposure to ultraviolet radiation, and when the second reminder message is pushed to the mobile terminal, the ultraviolet ray data of the current environment (UV numerical value information) is displayed by the corresponding applications of the mobile terminal. For another example, when the reminder messages are sent via the linear motor, different vibration frequencies may be set to reflect the difference between the first reminder and the second reminder, which is not limited here. A person skilled in the art may, according to the technical solution of the application in combination with a practical application scene, select a suitable numerical value and set it as the ultraviolet radiation threshold, for example, set 5~10 mJ/cm$^2$, which is recommended by the Chinese Clinical Medical Association, as the ultraviolet radiation threshold, which is not limited here.

In an embodiment of the application, the inertial sensor provided in the wearable device may also be used to monitor kinetic parameters in walking or running of the user, including stride frequency, touchdown time and touchdown balance of the right and left feet, and apparently the monitoring of kinetic parameters facilitates the user to better understand his/her sport performance efficiency, rectify running gesture and improve benefits of exercises. Moreover, the monitoring result data of the accelerometer and the gyroscope may also be used to judge whether the user tumbles. For example, when it is monitored that the variation of the acceleration of the wearable device within a preset unit time exceeds a first preset threshold range, and the variation of the rotational angular velocity of the wearable device within a preset unit time exceeds a second preset threshold range, it is determined that the user tumbles. At this point, a warning message may be sent to a smart phone by the Bluetooth communication module, the warning message comprises contact telephone numbers provided in advance, and the smart phone may be instructed to execute operations such as dialing the contact telephone numbers. The inertial sensor may use a nine-axis inertial sensor comprising a three-axis accelerometer, a three-axis gyroscope and a three-axis geomagnetic sensor, and the geomagnetic sensor provides direction reference for the gyroscope and the accelerometer.

Furthermore, the wearable device may also be provided with a barometer, and monitors the environmental air pressure data by using the barometer. When the variation of the environmental air pressure data within a certain duration exceeds a preset threshold, it is determined that the environment and weather are abnormal, and initiates a third alarm to the user, to prompt abnormal weathers such as storm. Furthermore, the barometer may also be used to monitor the height data of the head of the user, and the actions of the user that involve height variation such as sitting down, standing up and climbing stairs may be determined by the height data obtained by the barometer and the movement data obtained by the inertial sensor, which may be used to judge whether the user has been sitting for a long duration, and remind the user to notice if yes, and may also be used to count up the floor number climbed by a stair-climbing user and perform quantitative statistics of exercises.

Figure 5:
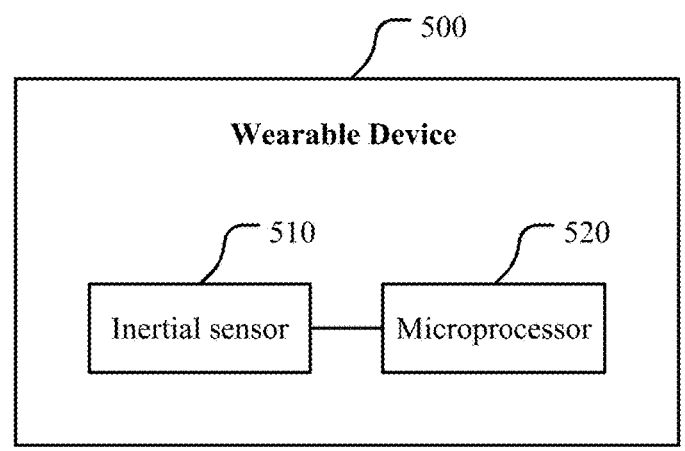
FIG. 5 shows a schematic diagram of a wearable device according to an embodiment of the application.

FIG. 5 shows a schematic diagram of a wearable device according to an embodiment of the application. As shown in FIG. 5, the wearable device 500, when being worn, is located on the head of a user, and comprises an inertial sensor 510 and a microprocessor 520.

The inertial sensor 510 is for monitoring movement data of the head of the user in real time when the user is wearing the wearable device 500.

The microprocessor 520 is connected to the inertial sensor 510, and is for conducting gesture solving by using the movement data, to obtain gesture data of the head of the user; judging whether a head gesture of the user is a correct gesture according to the gesture data and a preset strategy; and controlling to send a reminder to the user when it is determined that the head gesture of the user is an incorrect gesture.

It can be seen that, the wearable device 500 shown in FIG. 5 is worn on the head of the user, and monitors the movement data of the head of the user by using the inertial sensor 510, and the microprocessor 520 conducts gesture solving by using the monitored movement data to obtain gesture data of the head of the user, determines the head gesture of the user according to the gesture data and a preset strategy of the head of the user, and sends a reminder to the user when the head gesture of the user is incorrect. According to the present technical solution, the wearable device 500 is located on the head of the user, and the inertial sensor 510 provided in the wearable device 500 can maintain relatively stationary with respect to the head of the user, and can more accurately and efficiently monitor the movement data of the head of the user, and further obtain more authentic gesture data of the head of the user; it can realize effective monitoring of the head gesture of the user by analyzing the authentic gesture data of the head of the user, and send an alarm when the head gesture of the user is incorrect, to remind the user to notice the cervical vertebra health.

In an embodiment of the application, the wearable device 500 is smart glasses; the smart glasses comprise a spectacle frame and spectacle legs that are detachably connected to the spectacle frame, and both the inertial sensor 510 and the microprocessor 520 are provided in the spectacle legs.

In an embodiment of the application, the inertial sensor 510 comprises an accelerometer; the microprocessor 520 is connected to the accelerometer; the accelerometer is for measuring accelerations of the head of the user in x, y and z axis directions; and the microprocessor 520 is for conducting gesture solving by using the accelerations of the head of the user in the x, y and z axis directions, to obtain a pitch angle and a roll angle of the head of the user, and using the pitch angle and the roll angle as the gesture data of the head of the user.

Alternatively, the inertial sensor 510 comprises an accelerometer and a gyroscope; the microprocessor 520 is connected to the accelerometer and the gyroscope; the accelerometer is for measuring accelerations of the head of the user in x, y and z axis directions; the gyroscope is for measuring rotational angular velocities of the head of the user in the x, y and z axis directions; and the microprocessor 520 is for conducting gesture solving by using the accelerations of the head of the user in the x, y and z axis directions and the rotational angular velocities of the head of the user in the x, y and z axis directions, to obtain a pitch angle and a roll angle of the head of the user, and using the pitch angle and the roll angle as the gesture data of the head of the user;

where the x, y and z axes constitute a body coordinate system of the head of the user which varies along with movement of the head of the user, and in which the center of the head of the user is the origin of coordinates, the forward direction of the user's line of sight is the positive direction of the x axis, and the direction that points to a center of the head top of the user is the positive direction of the z axis, and the y axis together with the x axis and the z axis constitute a right-handed coordinate system.

On the basis that the microprocessor 520 obtained the gesture data of the head of the user, the microprocessor 520 is for presetting a balance threshold range; calculating a balance numerical value that indicates a balance degree of the movement of the head of the user according to the gesture data; and judging whether the balance numerical value exceeds the balance threshold range, and if yes, determining that the head gesture of the user is an incorrect gesture. Alternatively, the microprocessor 520 is for presetting a gesture data threshold range; judging whether the gesture data exceed the gesture data threshold range, and if yes, the head gesture of the user is determined as inappropriate; and determining that the head gesture of the user is an incorrect gesture if the inappropriate head gesture of the user maintains beyond a preset duration range.

Particularly, the microprocessor 520 is for presetting a first balance threshold range, and for each preset time cycle, accumulating each pitch angle of the head of the user that corresponds to each unit time within the preset time cycle, and using the numerical value obtained by the accumulating as the balance numerical value that corresponds to the pitch angles within the preset time cycle; and judging whether the balance numerical value that corresponds to the pitch angle exceeds the first balance threshold range, and if yes, determining that the head gesture of the user is an incorrect gesture. And/or, the microprocessor 520 is for presetting a second balance threshold range, and for each preset time cycle, accumulating each roll angle of the head of the user that corresponds to each unit time within the preset time cycle, and using the numerical value that is obtained by the accumulating as the balance numerical value that corresponds to the roll angles within the preset time cycle; and judging whether the balance numerical value that corresponds to the roll angle exceeds the second balance threshold range, and if yes, determining that the head gesture of the user is an incorrect gesture.

Figure 6:
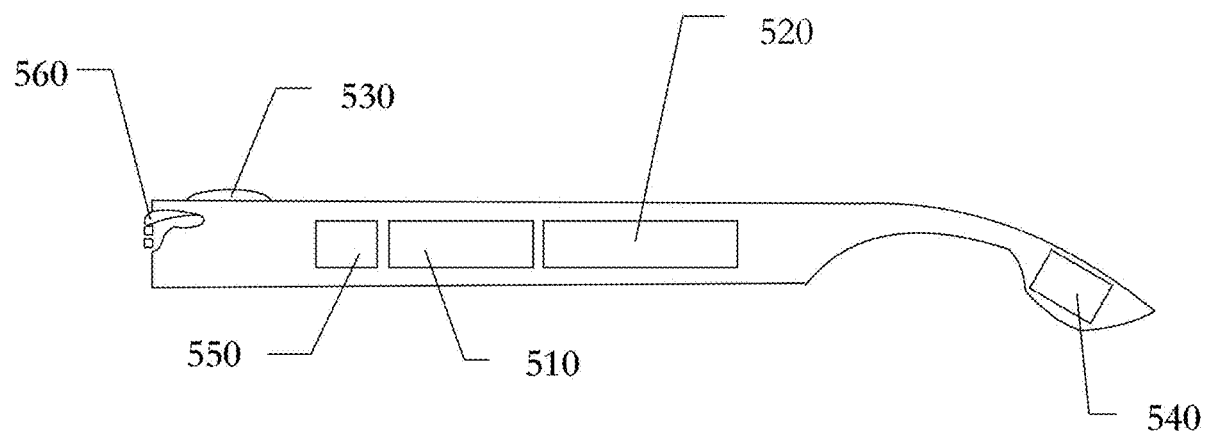
FIG. 6 shows a schematic diagram of spectacle legs of smart glasses according to an embodiment of the application.

FIG. 6 shows a schematic diagram of spectacle legs of smart glasses according to an embodiment of the application. As shown in FIG. 6, the spectacle legs comprise the inertial sensor 510 and the microprocessor 520 provided therein, and the principle of the interaction between the inertial sensor 510 and the microprocessor 520 has been explained above.

The spectacle legs are further provided therein with an ultraviolet sensor 530, and the ultraviolet sensor 530 is for monitoring environmental ultraviolet intensity, to obtain ultraviolet intensity data. The microprocessor 520 is further connected to the ultraviolet sensor 530, and is for presetting an ultraviolet radiation threshold, and sending a second reminder to the user when the ultraviolet intensity data exceed the ultraviolet radiation threshold.

The spectacle legs are further provided therein with a linear motor 540, and the microprocessor 520 is connected to the linear motor 540, and is for sending a reminder to the user via the vibration of the linear motor 540. The spectacle legs are further provided therein with a Bluetooth communication module 550, and the Bluetooth communication module 550 is for establishing the Bluetooth connection between the spectacle legs and the another mobile terminal; and the microprocessor 520 is connected to the Bluetooth communication module 550, and is for pushing a reminder message to the another mobile terminal via the Bluetooth connection.

The spectacle connection part 560 of the spectacle legs is adapted for various spectacle frames. The user may replace the spectacle frame without replacing the spectacle legs according to his/her own demands. The spectacle legs and the spectacle frame constitute the whole smart glasses. Furthermore, the spectacle legs are further provided therein with modules such as a battery, and may also use wireless charging technique, to ensure performance of the product.

In an embodiment of the application, the microprocessor 520 detects whether the smart glasses are in the state of being worn. Particularly, the accelerometer in the inertial sensor 510 monitors the acceleration of the smart glasses in real time, and the microprocessor 520 calculates the amplitude value of the acceleration of the smart glasses, and judges whether variation within a preset duration of an amplitude value of the acceleration of the smart glasses exceeds the wearing detecting threshold, and if yes, determines that the smart glasses legs are in the state of being worn.

It should be noted that, the embodiments of the device shown in FIG. 5 to FIG. 6 are correspondingly the same as the embodiments shown above in FIG. 1 to FIG. 4, which are illustrated in detail above and not repeated here.

In conclusion, in the technical solution provided by the application, the movement data of the head of the user are monitored by using the wearable device worn on the head of the user; gesture solving is conducted to the monitored movement data to obtain gesture data of the head of the user; the head gesture of the user is determined according to the gesture data and a preset strategy of the head of the user, and when the head gesture of the user is incorrect, a reminder is sent to the user. According to the present technical solution, the following can be achieved. Namely, first, ultraviolet ray is monitored by monitoring the ultraviolet intensity in the environment in real time by using the ultraviolet sensor provided in the spectacle legs, and sending an alarm to the user when the ultraviolet intensity is too high; second, the head gesture is monitored by conducting gesture solving by using the head gesture of the user by using the inertial sensor and the barometer that are built in the spectacle legs, the head gesture of the user is monitored in real time, and an alarm is sent to the user when the head of the user is in the tilting gesture for a long duration. In addition, most current glasses-type smart wearable devices are integral spectacle frames, or products of the sport goggles type. However, with the individuality pursuing trend today, glasses, as a product worn on the face, are usually the first target to be personalized for people pursuing individuality. The spectacle legs and the spectacles frame of the application are detachably connected, and the connection parts are standard components and can match most of the glasses in the current market, thus the user can enjoy the convenience brought by the smart device without replacing the glasses.

The above description is merely preferable embodiments of the application, and is not used to limit the protection scope of the application. Any modifications, equivalent substitutions or improvements that are made within the spirit and principle of the application are all included in the protection scope of the application.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment, it being understood that various changes may be made in the function and arrangement of elements described in an exemplary embodiment without departing from the scope of the invention as set forth in the appended claims and their legal equivalents.

What is claimed is:

1. A method for monitoring a user gesture, wherein the method comprises the steps of:
   providing an inertial sensor in a wearable device, the wearable device being located on the head of a user when being worn;
   monitoring movement data of the head of the user in real time, by using the inertial sensor, when the user is wearing the wearable device;
   conducting gesture solving by using the movement data to obtain gesture data of the head of the user; and determining whether a head gesture of the user is a correct gesture according to the gesture data and a preset strategy; and
   sending a reminder to the user when the head gesture of the user is an incorrect gesture;
   the inertial sensor comprises an accelerometer;
   the step of monitoring movement data of the head of the user in real time by using the inertial sensor comprises: measuring accelerations of the head of the user in x, y and z axis directions by using the accelerometer; and
   the step of conducting gesture solving by using the movement data to obtain gesture data of the head of the user comprises:
   conducting gesture solving by using the accelerations of the head of the user in the x, y and z axis directions to obtain a pitch angle and a roll angle of the head of the user, and using the pitch angle and the roll angle as the gesture data of the head of the user;
   wherein the x, y and z axes constitute a body coordinate system of the head of the user which varies along with movement of the head of the user, and in which the center of the head of the user is the origin of coordinates, the forward direction of the user's line of sight is the positive direction of the x axis, and the direction that points to a center of the head top of the user is the positive direction of the z axis, and the y axis together with the x axis and the z axis constitute a right-handed coordinate system;
   the step of determining whether a head gesture of the user is a correct gesture according to the gesture data and a preset strategy comprises the steps of:
   presetting a balance threshold range; calculating a balance numerical value that indicates a balance degree of the movement of the head of the user according to the gesture data; and judging whether the balance numerical value exceeds the balance threshold range, and if yes, determining that the head gesture of the user is an incorrect gesture;
   the steps of presetting a balance threshold range; calculating a balance numerical value that indicates a balance degree of the movement of the head of the user according to the gesture data; and judging whether the balance numerical value exceeds the balance threshold range, and if yes, determining that the head gesture of the user is an incorrect gesture comprise:
   presetting a first balance threshold range, and for each preset time cycle, accumulating each pitch angle of the head of the user that corresponds to each unit time within the preset time cycle, and using the numerical value obtained by the accumulating as the balance numerical value that corresponds to the pitch angles within the preset time cycle; and judging whether the balance numerical value that corresponds to the pitch angle exceeds the first balance threshold range, and if yes, determining that the head gesture of the user is an incorrect gesture;
   and/or,
   presetting a second balance threshold range, and for each preset time cycle, accumulating each roll angle of the head of the user that corresponds to each unit time within the preset time cycle, and using the numerical value obtained by the accumulating as the balance numerical value that corresponds to the roll angles within the preset time cycle; and judging whether the balance numerical value that corresponds to the roll angle exceeds the second balance threshold range, and if yes, determining that the head gesture of the user is an incorrect gesture.

2. The method according to claim 1, wherein the wearable device is smart glasses; and the smart glasses comprise a spectacle frame and spectacle legs that are detachably connected to the spectacle frame, and the inertial sensor and a microprocessor are provided in the spectacle legs.

3. The method according to claim 1, wherein the inertial sensor further comprises a gyroscope;
   the step of monitoring movement data of the head of the user in real time by using the inertial sensor further comprises: measuring rotational angular velocities of the head of the user in the x, y and z axis directions by using the gyroscope; and the step of conducting gesture solving by using the movement data to obtain gesture data of the head of the user comprises: conducting gesture solving by using the accelerations of the head of the user in the x, y and z axis directions and the rotational angular velocities of the head of the user in the x, y and z axis directions, to obtain the pitch angle and the roll angle of the head of the user, and using the pitch angle and the roll angle as the gesture data of the head of the user.

4. The method according to claim 1, wherein providing an ultraviolet sensor in the wearable device; and the method further comprises:

monitoring environmental ultraviolet intensity by using the ultraviolet sensor, to obtain ultraviolet intensity data; presetting an ultraviolet radiation threshold; and sending a second reminder to the user when the ultraviolet intensity data obtained exceed the ultraviolet radiation threshold.

5. The method according to claim 1, wherein before the step of monitoring movement data of the head of the user in real time by using the inertial sensor, the method further comprises:

presetting a wearing detecting threshold; and monitoring the acceleration of the wearable device in real time by using the accelerometer, judging whether the variation within a preset duration of an amplitude value of the acceleration of the wearable device exceeds the wearing detecting threshold, and if yes, determining that the wearable device is in the state of being worn, and then executing the step of monitoring movement data of the head of the user in real time by using the inertial sensor;

the wearable device is further provided with a linear motor and/or a Bluetooth communication module; and the step of sending a reminder to the user comprises: sending a reminder to the user by vibration of the linear motor, and/or, connecting to another mobile terminal by using the Bluetooth communication module, and pushing a reminder message to the another mobile terminal.

6. A wearable device, wherein the wearable device being located on the head of a user when being worn, and comprises an inertial sensor and a microprocessor;

the inertial sensor is for monitoring movement data of the head of the user in real time when the user is wearing the wearable device; and the microprocessor is connected to the inertial sensor, and is for conducting gesture solving by using the movement data to obtain gesture data of the head of the user, determining whether a head gesture of the user is a correct gesture according to the gesture data and a preset strategy, and is controlled to send a reminder to the user when it is determined that the head gesture of the user is an incorrect gesture;

the inertial sensor comprises an accelerometer;

the microprocessor is connected to the accelerometer;

the accelerometer is for measuring accelerations of the head of the user in x, y and z axis directions;

the microprocessor is for conducting gesture solving by using the accelerations of the head of the user in the x, y and z axis directions, to obtain a pitch angle and a roll angle of the head of the user, and using the pitch angle and the roll angle as the gesture data of the head of the user;

wherein the x, y and z axes constitute a body coordinate system of the head of the user which varies along with movement of the head of the user, and in which the center of the head of the user is the origin of coordinates, the forward direction of the user's line of sight is the positive direction of the x axis, and the direction that points to a center of the head top of the user is the positive direction of the z axis, and the y axis together with the x axis and the z axis constitute a right-handed coordinate system;

the microprocessor is for presetting a balance threshold range; calculating a balance numerical value that indicates a balance degree of the movement of the head of the user according to the gesture data; and judging whether the balance numerical value exceeds the balance threshold range, and if yes, determining that the head gesture of the user is an incorrect gesture;

the microprocessor is for presetting a first balance threshold range, and for each preset time cycle, accumulating each pitch angle of the head of the user that corresponds to each unit time within the preset time cycle, and using the numerical value obtained by the accumulating as the balance numerical value that corresponds to the pitch angles within the preset time cycle; and judging whether the balance numerical value that corresponds to the pitch angle exceeds the first balance threshold range, and if yes, determining that the head gesture of the user is an incorrect gesture;

and/or, presetting a second balance threshold range, and for each preset time cycle, accumulating each roll angle of the head of the user that corresponds to each unit time within the preset time cycle, and using the numerical value obtained by the accumulating as the balance numerical value that corresponds to the roll angles within the preset time cycle; and judging whether the balance numerical value that corresponds to the roll angle exceeds the second balance threshold range, and if yes, determining that the head gesture of the user is an incorrect gesture.

7. The wearable device according to claim 6, wherein the wearable device is smart glasses; and the smart glasses comprise a spectacle frame and spectacle legs that are detachably connected to the spectacle frame, and the inertial sensor and the microprocessor are provided in the spectacle legs.

8. The wearable device according to claim 7, wherein the inertial sensor further comprises a gyroscope;

the microprocessor is connected to the accelerometer and the gyroscope respectively;

the accelerometer is for measuring accelerations of the head of the user in x, y and z axis directions;

the gyroscope is for measuring rotational angular velocities of the head of the user in the x, y and z axis directions; and the microprocessor is for conducting gesture solving by using the accelerations of the head of the user in the x, y and z axis directions and the rotational angular velocities of the head of the user in the x, y and z axis directions, to obtain a pitch angle and a roll angle of the head of the user, and using the pitch angle and the roll angle as the gesture data of the head of the user.

9. The wearable device according to claim 8, wherein the accelerometer is further for monitoring the acceleration of the wearable device in real time;

the microprocessor is further for presetting a wearing detecting threshold, judging whether variation within a preset duration of an amplitude value of the acceleration of the wearable device exceeds the wearing detecting threshold, and if yes, determining that the wearable device is in the state of being worn; and the accelerometer monitors the movement data of the head of the user in real time after it is determined that the wearable device is in the state of being worn.

10. The wearable device according to claim 7, wherein
an ultraviolet sensor is further provided in the spectacle legs, and the ultraviolet sensor is for monitoring environmental ultraviolet intensity to obtain ultraviolet intensity data; and
the microprocessor is further connected to the ultraviolet sensor, and is for presetting an ultraviolet radiation threshold, and sending a second reminder to the user when the ultraviolet intensity data exceed the ultraviolet radiation threshold.

11. The wearable device according to claim 7, wherein
a linear motor and/or a Bluetooth communication module are/is further provided in the spectacle legs;
the microprocessor is connected to the linear motor, and is for sending a reminder to the user by vibration of the linear motor; and
the microprocessor is connected to the Bluetooth communication module, and is for connecting to another mobile terminal by using the Bluetooth communication module, and pushing a reminder message to the another mobile terminal.

* * * * *